(12) United States Patent
Mahler (10) Patent No.: US 8,286,285 B2
(45) Date of Patent: Oct. 16, 2012

(54) ORTHOPEDIC SUPPORT PILLOW (76) Inventor: Sheila J. Mahler, Orange Village, OH (US)

( * ) Notice: Subject to any disclaimer, the term of this patent is extended or adjusted under 35 U.S.C. 154(b) by 0 days.

(21) Appl. No.: 13/135,752

(22) Filed: Jul. 15, 2011

(65) Prior Publication Data

US 2012/0131751 A1     May 31, 2012

Related U.S. Application Data

(63) Continuation-in-part of application No. PCT/US2010/002594, filed on Sep. 21, 2010.

(60) Provisional application No. 61/277,049, filed on Sep. 21, 2009.

(51) Int. Cl.
*A61G 7/075* (2006.01)
*A47C 16/00* (2006.01)

(52) U.S. Cl. ............... 5/646; 5/647; 5/655.3; 128/878

(58) Field of Classification Search .......... 5/646, 647, 5/655.3, 490; 128/877, 878; 602/20
See application file for complete search history.

(56) References Cited

U.S. PATENT DOCUMENTS

| | | | |
|---|---|---|---|
| 4,270,235 A * | 6/1981 | Gutmann | 5/646 |
| 4,598,701 A | 7/1986 | Schaefer | |
| 4,896,660 A | 1/1990 | Scott | |
| 5,012,539 A * | 5/1991 | Grigg | 5/644 |
| D317,840 S | 7/1991 | Jagdat | |
| 5,173,979 A * | 12/1992 | Nennhaus | 5/648 |
| 5,665,058 A | 9/1997 | Young | |
| 6,691,353 B2 * | 2/2004 | Fuhriman | 5/646 |
| 6,932,781 B2 | 8/2005 | Itoi | |
| 7,017,215 B1 | 3/2006 | Singer et al. | |
| 7,244,239 B2 | 7/2007 | Howard | |
| 7,441,293 B1 | 10/2008 | Singer et al. | |
| 7,563,236 B2 | 7/2009 | Kazmierczak et al. | |
| 7,640,610 B2 * | 1/2010 | Mervar | 5/647 |
| 8,043,241 B2 * | 10/2011 | Goumas | 602/4 |
| 2009/0119845 A1 * | 5/2009 | Bastien et al. | 5/646 |

* cited by examiner

*Primary Examiner* — Michael Trettel
(74) *Attorney, Agent, or Firm* — Gerald R. Black (57) ABSTRACT

The orthopedic support pillow is for use by a patient having a retained arm while the patient is lying in a generally prone position sideways on a resting surface. The orthopedic support pillow comprises two side surfaces, the two side surfaces opposing each other, and a bracing surface. The second side surface accommodates the retained arm of the patient and is at least as wide as the ailing forearm of the patient. The bracing surface is disposed between the two side surfaces, and has a generally concave shape. The abdominal section of the patient abuts against the bracing surface of the orthopedic support pillow when the patient is lying in the prone position sideways. The orthopedic support pillow provides stability and support to the retained arm in an elevated position while the patient is in the generally prone position on the resting surface. The orthopedic support pillow includes a strap or pocket positioned for retaining the hand of retained arm of the patient. The orthopedic support pillow is either made of a resilient foam material, or has an inflatable pillow body with an interior that is adapted to be filled with air inflate the pillow body, enabling firmness of the orthopedic support pillow to be adjusted for comfort by each patient.

20 Claims, 11 Drawing Sheets

ORTHOPEDIC SUPPORT PILLOW

This Application is a continuation-in-part and claims priority to PCT Application PCT/US2010/02594, entitled "Orthopedic Support Pillow", filed on Sep. 21, 2010; which claims priority to U.S. Provisional Application No. 61/277,049, filed on Sep. 21, 2009.

FIELD OF USE

This invention relates to an orthopedic support pillow to be used by a patient to support an arm of the patient while resting in a generally prone position on one side with the retained arm elevated and supported in a stable position.

BACKGROUND OF THE INVENTION

All musculoskeletal problems related to the neck, upper extremities, and shoulders. For example, the "rotator cuff" is the group of muscles and their tendons that act to stabilize the shoulder. The rotator cuff muscles are important in shoulder movements and in maintaining shoulder joint stability.

One of the most important things is to treat rotator cuff injury as soon as possible. The initial 48-72 hours are vital for a speedy recovery and complete. The conventional medical treatment as soon as injury occurs is rest, ice, compression, elevation, and referral.

Deciding on when a torn rotator cuff will need surgical intervention is dependent on how the injury responds to other treatments. If other forms of non-surgical treatments prove to be ineffective even after a number of months, rotator cuff surgery may be needed.

Whether or not surgery is needed, bed rest and elevation of the retained arm are critical to the well-being and the recovery of the patient.

A search of the prior art discloses some prior art devices that are known that may be useful.

U.S. Pat. No. 7,563,236 (Kazmierczak, et al.) discloses a shoulder sling for the treatment of, for example, glenohumeral dislocations and subluxations, capsular shifts, postoperative rotator cuff repair, postoperative Bankart procedures and soft tissue strains and repairs. The sling includes a support pillow abuts the wearer's torso, and a pouch that receives the wearer's arm. A plurality of straps suspend the pillow and pouch from the wearer's non-treatment shoulder. One of the straps prevents the pillow from shifting relative to the patient, thus securely maintaining the wearer's arm at desired angles of abduction and external rotation. The pillow further includes an attached exercise grip and an indicator line that aids a physician in properly fitting the sling to the wearer.

U.S. Pat. No. 7,441,293 (Singer, et al.) discloses a support for a lower shoulder and extended arms of a person tying on their side. One embodiment comprises a set of three stacked cushions to support a lower shoulder and both extended arms of a patient in a lateral and semi-lateral position on a bed. A bottom cushion has a flat compressible surface to support the patients lower shoulder and a middle cushion. Smaller middle and top cushions stack on the bottom cushion. The middle and top cushions each comprises a top surface with a furrow for support and access to the arms. In addition, the middle and top cushions have cut-off corners that provide access to the person's nasopharyngeal cavities.

U.S. Pat. No. 7,017,215 (Singer, et al.) discloses a support for extended arms of a person tying on his or her side. A bottom cushion and a top cushion are rectangular and have top furrows so that when stacked they can support and provide access to the arms generally perpendicular to a patient lying on their side. In addition the bottom cushion and the top cushion have cut-off corners, respectively, which align to provide access to the nasal and oral cavities during surgical procedures performed in these positions.

U.S. Pat. No. 6,932,781 (Itoi) discloses a shoulder dislocation acute-phase immobilization orthosis that is used a shoulder dislocation acute-phase immobilization orthosis for supporting, in treatment for a shoulder dislocation, an arm in a prescribed position while the elbow is bent at a right angle in an arm hanging position. The orthosis comprises a support frame integrally formed of a lightweight hard thick-plated material, with a width approximately greater than that of the forearm, comprising: a curved portion which follows the shape of the abdominal part of a body and an arm supporting side face of approximately the forearm length, which is integrally extended forward from one end of the curved portion via a bent portion and is bent at an appointed angle; an arm supporting member(s) for immobilizing the forearm, provided on the arm supporting side face of the support frame; and a wrap-around belt made of a flexible material having a width identical to that of the support frame, provided with a surface fastener for fitting the support frame to the trunk part of a body.

U.S. Pat. No. 4,896,660 (Scott) discloses an arm elevation support device comprising a generally monolithic humerus support, a contoured well shoulder anchor, and a radius and ulna support. The monolithic humerus support is operable to abut against a patients side and underlies the humeral portion of a patients arm. The contoured well shoulder anchor includes a contoured sleeve portion operable to be worn around the acromial portion of a patients well arm and two straps which releasably connect the well shoulder anchor to the monolithic humerus support. The radius and ulna support connects to the monolithic structure and provides support for a patients forearm and hand.

U.S. Pat. No. 4,598,701 (Schaefer) discloses a shoulder abduction splint constructed from a unitary block of synthetic foam material is illustrated providing in a single disposable support a splint for selectively positioning the arm in a substantially 90 degree position with respect to the body or an intermediate position with respect to the body as dictated by the results of surgery on the shoulder.

U.S. Pat. No. D317,840 (Jagdat) discloses an ornamental design for a pillow, although there is no indication as to how the pillow is to be used.

U.S. Provisional Application No. 61/277,049, entitled "Orthopedic Support Pillow" (Mahler, discloses an orthopedic support pillow is for use by a patient having a retained arm while the patient is lying in a generally prone position sideways on a resting surface. The orthopedic support pillow comprises two side surfaces, the two side surfaces opposing each other, and a bracing surface. The bracing surface is disposed between the two side surfaces, and abuts the abdominal section of the patient when the patient is lying in the prone position sideways. The orthopedic support pillow provides stability and support to the retained arm in an elevated position while the patient is in the generally prone position on the resting surface.

In addition, prior art is also known that enables a user to adjust the amount of support provided by a pillow.

U.S. Pat. No. 7,634,829 (La Bar) discloses a self-contained head and chest support kit for indoor and outdoor use, which allows a patient to support his head and chest for comfort, the kit consisting of a head and chest pillow, a head pillow cover, a chest pillow cover, an adjustment strap, an air pump to inflate the head pillow and the chest pillow, and a convenient storage bag. During use for sunbathing, the head pillow supports the forehead, while the chest pillow keeps the patients spine in prior alignment, thereby also elevating the face away from the sand or ground and preventing the face from burning due to overexposure from the sun. When used for sleeping, the head pillow and chest pillow allow the neck and back muscles to lie in a more relaxed position and create a better posture. Use of the pillows in the present kit helps alleviate tension in the neck and back muscles.

U.S. Pat. No. 6,951,038 (Ganoe) discloses an adjustable air pillow for the head, neck, and spine includes an internal air bladder that can be incrementally inflated and deflated so that a conformable padding with a recessed upper surface that completely encloses the air bladder can support and elevate the individual's head, neck and spine for obtaining the proper alignment thereof for rest, relaxation or sleep. The incremental inflation and deflation of the air bladder is controlled from a control box that encloses an air pump interconnected to the air bladder by a flexible air line, and the control box can be powered by batteries or by plugging the control box into a standard wall outlet for being powered by normal house current.

U.S. Pat. No. 6,131,219 (Roberts) discloses an inflatable pillow has an air-impervious flexible bladder with one or more chambers therein which are inflatable to different shapes, thicknesses and firmness to conform the pillow to the requirements of different individuals. A soft cover is removably placed on the bladder to enhance the comfort and appearance of the pillow, and the cover is removable for cleaning. In one form of the invention, opposite ends of the pillow are recessed to provide clearance for the face of a person using the pillow, when the person is lying on his or her side. A cervical support portion of increased thickness or firmness extends along a front edge of the pillow.

What is needed is an orthopedic support pillow that will alleviate musculoskeletal problems related to the neck, upper extremities, and shoulders, enabling ailing and recovering patients to rest comfortably while lying in a prone position, either on the patient's back or side while elevating a retained arm and experiencing some relief.

What is needed is an orthopedic support pillow that will provide support for an aging population suffering from arthritis in the shoulders, neck, back, and upper extremities to rest comfortably and adjust the support that the orthopedic support pillow provides over an entire range of the retained arm.

More specifically, what is needed is an orthopedic support pillow that will provide support for a person with an ailing rotator cuff, to elevate such arm while reclining in a prone position with such arm elevated and supported, in a stable position, enabling such person to rest comfortably for extended periods of time.

SUMMARY OF THE INVENTION

The orthopedic support pillow of the present invention addresses these needs.

The orthopedic support pillow is for use by a patient having a retained arm while the patient is lying in a generally prone position either on one's back or side on a resting surface. The orthopedic support pillow comprises two side surfaces, the two side surfaces opposing each other, and a bracing surface. The second side surface accommodates the retained arm of the patient and is at least as wide as the forearm of the patient. The bracing surface is disposed between the two side surfaces, and has a generally concave shape. The abdominal section of the patient abuts against the bracing surface of the orthopedic support pillow when the patient is lying in the prone position sideways.

The orthopedic support pillow provides stability and support to the retained arm in an elevated position while said patient is in said generally prone position on said resting surface. The orthopedic support pillow includes an adjustable strap or pocket positioned for retaining the hand of retained arm of the patient. The orthopedic support pillow is either made of a resilient foam material, or has an inflatable pillow body with an interior that is adapted to be filled with air inflate the pillow body, enabling firmness of the orthopedic support pillow to be adjusted for comfort by each patient.

One preferred embodiment includes a manually operable control means for selectively discharging fluid into a fluid chamber for inflating a bladder and increasing the height and firmness of the orthopedic support pillow of the present invention. Excess fluid can be selectively evacuated fluid from the fluid chamber deflating the bladder and thereby decreasing height and firmness of the orthopedic support pillow. The incremental inflation and deflation of the bladder is controlled from a control box. The control box is powered either by batteries or by plugging the control box into a standard wall outlet and powered by normal house current.

For a more complete understanding of the orthopedic support pillow of the present invention, reference is made to the following detailed description and accompanying drawings in which the presently preferred embodiments of the invention are shown by way of example. As the invention may be embodied in many forms without departing from spirit of essential characteristics thereof, it is expressly understood that the drawings are for purposes of illustration and description only, and are not intended as a definition of the limits of the invention. Throughout the description, like reference numbers refer to the same component throughout the several views.

BRIEF DESCRIPTION OF THE DRAWINGS

FIG. 3 depicting the topside of the orthopedic support pillow, the patient is resting in a generally prone position on a resting surface.

FIG. 5 depicting the patient resting in a generally prone position on her back with her arm in an elevated and stable position on the top surface, her hand being secured under the strap.

DETAILED DESCRIPTION OF THE PREFERRED EMBODIMENTS

Figure 1A:
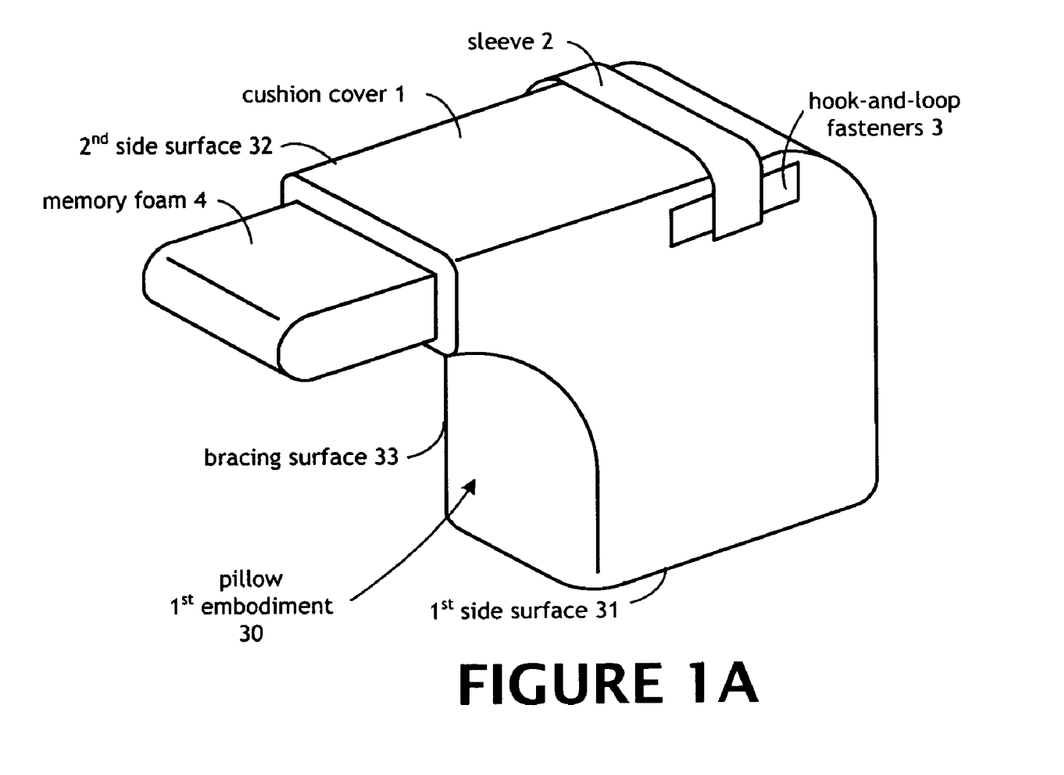
FIG. 1A discloses a first preferred embodiment of the orthopedic support pillow of the present invention comprising an upper and a lower surface and a bracing surface with a strap positioned on the top surface for retaining a hand of a patient using the orthopedic support pillow, the orthopedic support pillow having a resilient upholstery memory foam and a coating.
Figure 1B:
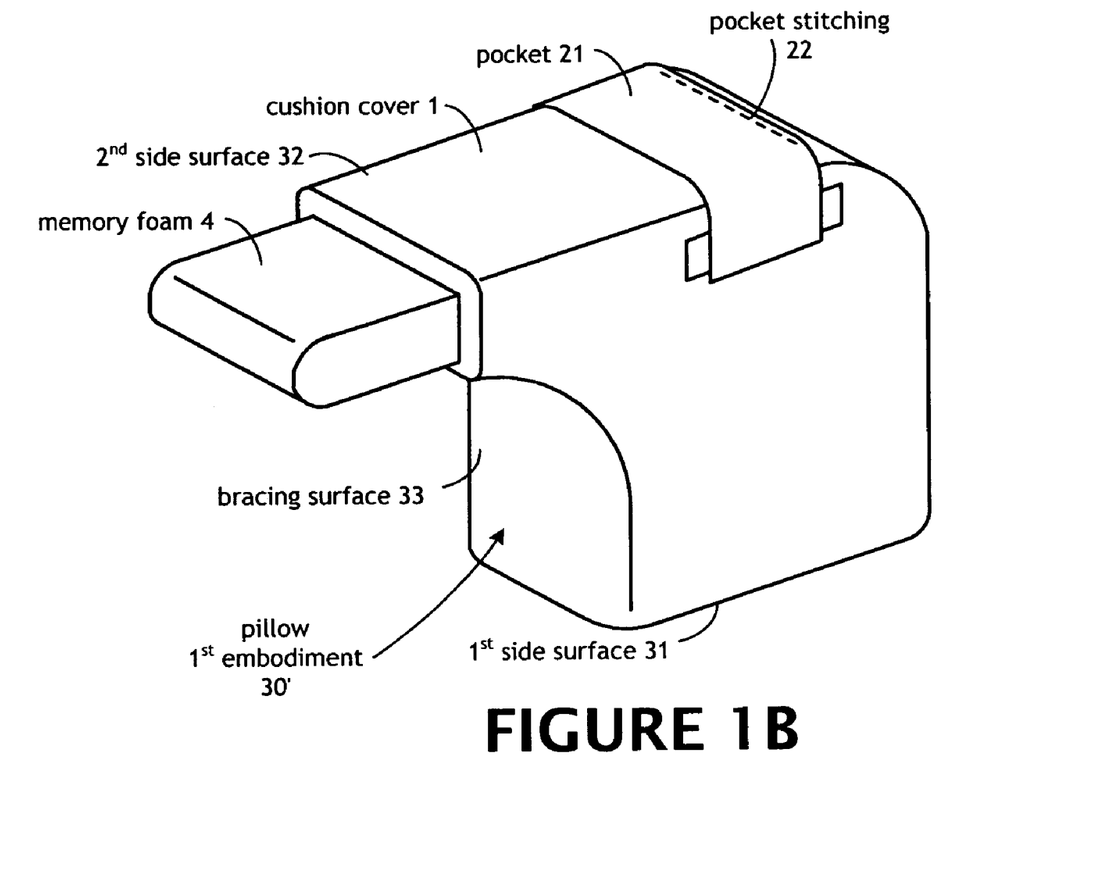
FIG. 1B discloses a variation of the first preferred embodiment of the orthopedic support pillow of the present invention where there is and a bracing surface with a pocket positioned on the top surface for retaining a hand of a patient using the orthopedic support pillow.
Figure 2:
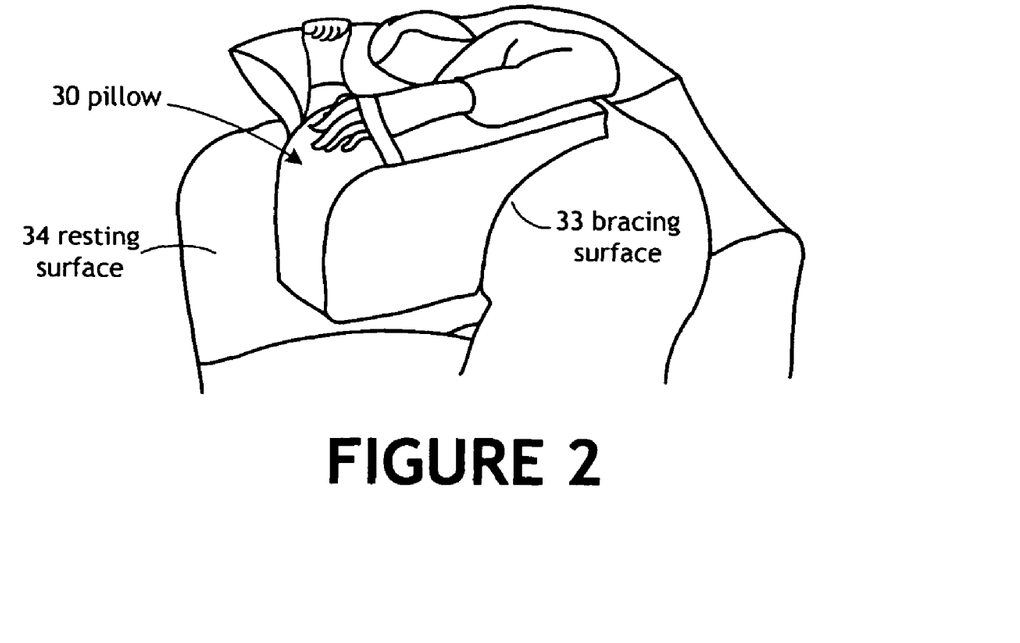
FIGS. 2 and 3 disclose the preferred embodiment of the orthopedic support pillow of FIG. 1A in use by a patient, FIG. 2 depicting the underside of the orthopedic support pillow, the patient is resting in a generally prone position on a resting surface.
Figure 3:
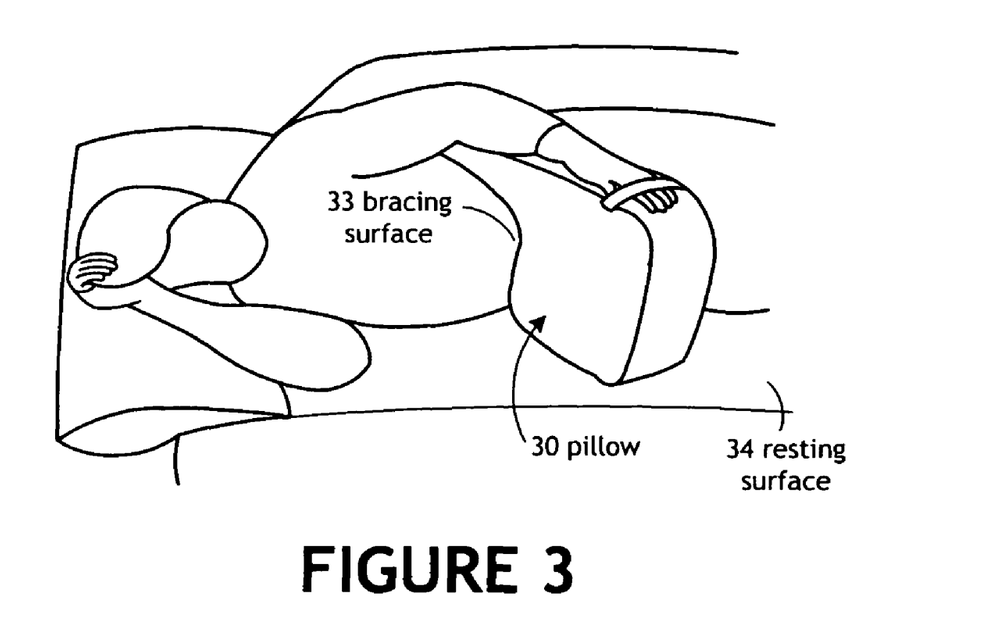
Figure 4:
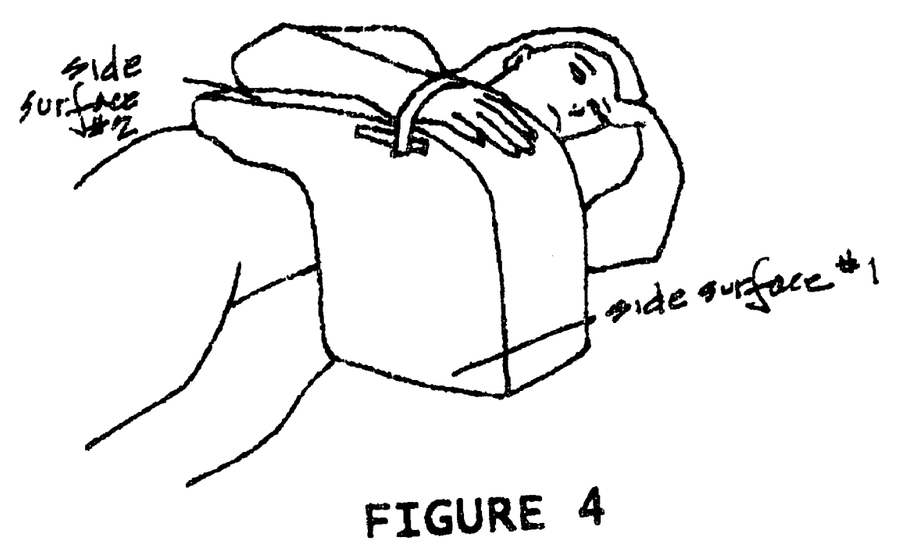
FIGS. 4 and 5 disclose the preferred embodiment of the orthopedic support pillow of FIG. 1A in use by a patient, FIG. 4 depicting the patient resting in a generally prone position on a side with the arm in an elevated and stable position on the top surface, her hand being secured under the strap.

Referring now to the drawings, FIGS. 1A and 1B disclose the first preferred embodiments of the orthopedic support pillow of the present invention 30. The orthopedic support pillow 30 comprises a pair of side surfaces. When the patient is resting on a side, with the ailing arm elevated (see FIGS. 2, 3, and 4), a first side surface 31 is positioned on the resting surface 34 upon which the patient is lying. The second side surface 32 is preferably parallel to the first side surface 31. The arm of the patient is positioned on the second side surface 32 keeping in mind that the ailing arm is preferably not to be extended away from the shoulder, but only the forearm from the elbow to the hand.

The abdominal section of the patient abuts against the bracing surface 33 of the orthopedic support pillow of the present invention 30. This will keep the ailing arm elevated and enable the patient to rest and perhaps even sleep. The hand of the patient is retained in a strap or sleeve 2 that extends across the second side surface 32 and can be tightened or loosened by attachment to hook-and-loop fasteners (preferably Velcro®) 3, as depicted in FIG. 1A. FIG. 1B depicts another embodiment of the orthopedic support pillow 30' having a pocket 21 stitched to the second side surface 32, the stitched pocket 21 replacing the adjustable sleeve 2.

The first two preferred embodiments of the orthopedic support pillow of the present invention 30 and 30' are made of heavy density, firm and extra firm upholstery foam rubber having memory. The foam 4 of choice is designated as "1545 firm foam", which is commercially available from Ohio Foam located at 820 Bucyrus, Ohio. The covering 1 is made of a material that to cover and protect the foam material. The cover is designed for durability and cleanliness. The strap attachment areas are preferably positioned on the cushion cover 1 rather than on the cushion 4. The cushion cover 1 preferably includes a zipper (not shown). When the zipper is open, the cushion cover 1 may be removed from around the orthopedic support pillow of the present invention for cleaning or replacement of the cover or of the orthopedic support pillow. Other resilient synthetic polymeric foam material with memory, such as a closed cell foam material commonly known in the art for making cushions, may also be deployed.

Figure 5:
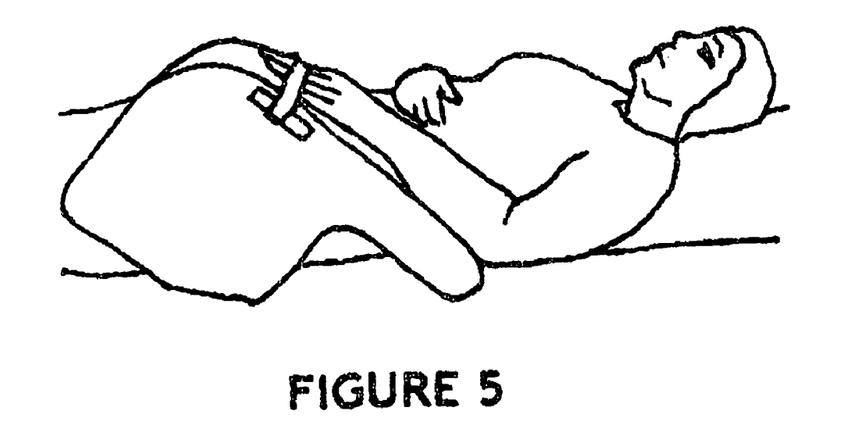

Certain patients prefer to rest on their backs, and depending upon the medical condition, this position may be preferred to a sideways position. FIG. 5 depicts a patient resting in a generally prone position on her back with her arm in an elevated and stable position on the second side surface 32 of the orthopedic support pillow of the present invention 30, the patient's hand being secured under the strap 2. Also, it is advantageous that the orthopedic support pillow of the present invention 30 enables the patient to sleep either on her back or on her side while supporting and elevating the ailing arm in a stable position.

Figure 6:
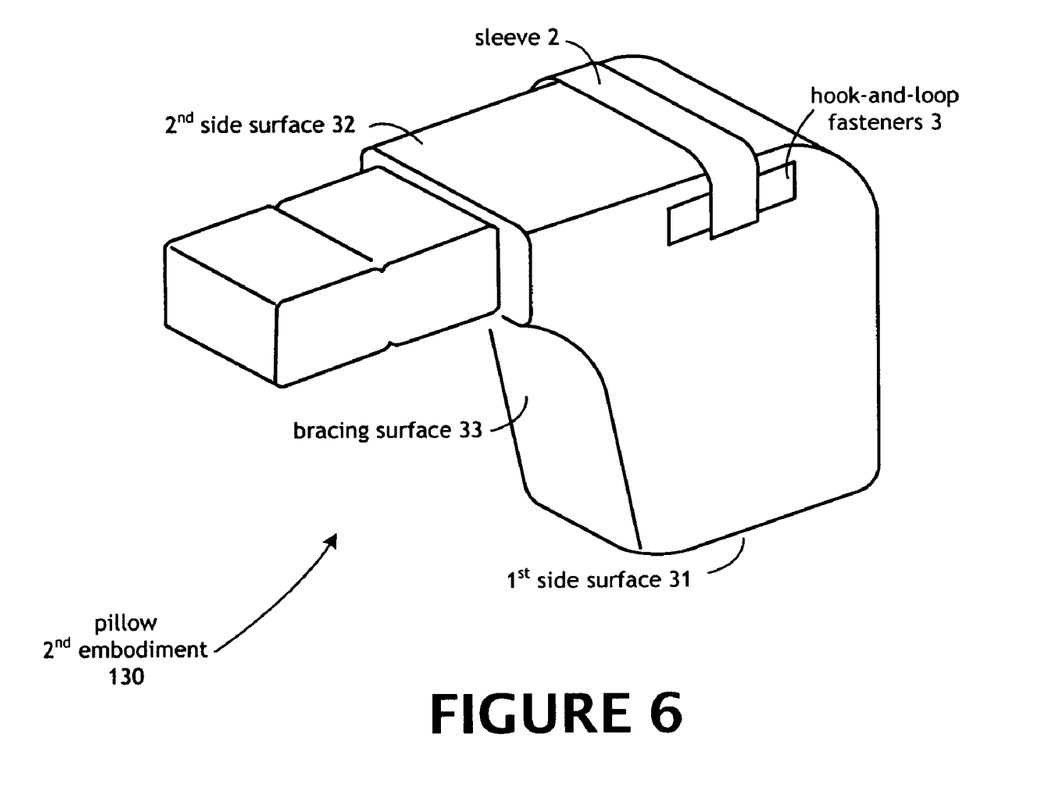
FIG. 6 discloses another preferred embodiment of the orthopedic support pillow of the present invention comprising an upper and a lower surface and a bracing surface with a strap positioned on the top surface for retaining a hand of a patient using the orthopedic support pillow, the orthopedic support pillow being comprised of multiple inflatable bladders that enable adjustment of firmness for comfort for the patient, the multiple inflatable bladders having bladder sections that are normal to the axis of the bracing surface.

FIG. 6 discloses another preferred embodiment of the orthopedic support pillow of the present invention 130. In this embodiment, the orthopedic support pillow 130 is comprised of multiple inflatable bladders that enable adjustment of firmness for comfort for the patient. If the condition of the patient improves, less support may be needed. If the condition of the patient deteriorates, more support may be needed. If the particular condition is a recurring one, adjustment is also necessary. The multiple inflatable bladders 5 include bladder sections that are aligned with the axis of the strap 2.

Figure 7A:
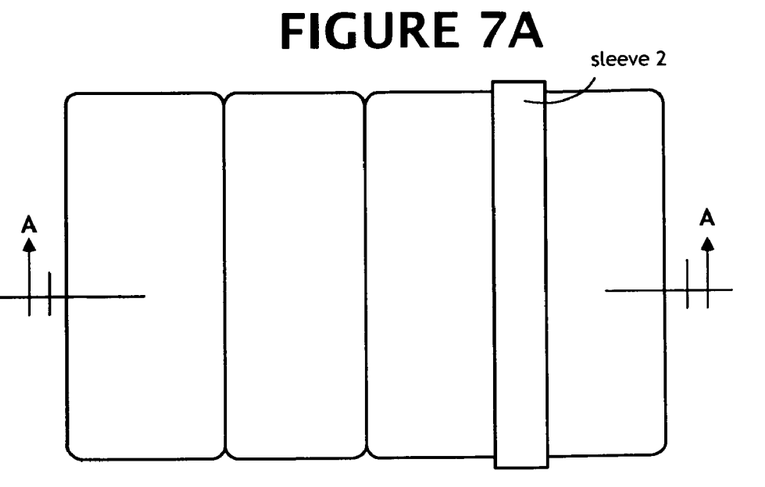
FIGS. 7A and 7B disclose still another preferred embodiment of the orthopedic support pillow of FIG. 6, FIG. 7A depicting a top view of the orthopedic support pillow, and FIG. 7B depicting a Section A-A taken through FIG. 7A, the orthopedic support pillow comprising an upper and a lower surface and a bracing surface with a strap positioned on the top surface for retaining a hand of a patient using the orthopedic support pillow, the orthopedic support pillow being comprised of multiple inflatable bladders that enable adjustment of firmness for comfort for the patient, the multiple inflatable bladders having bladder sections that are axially aligned with the support strap.
Figure 7B:
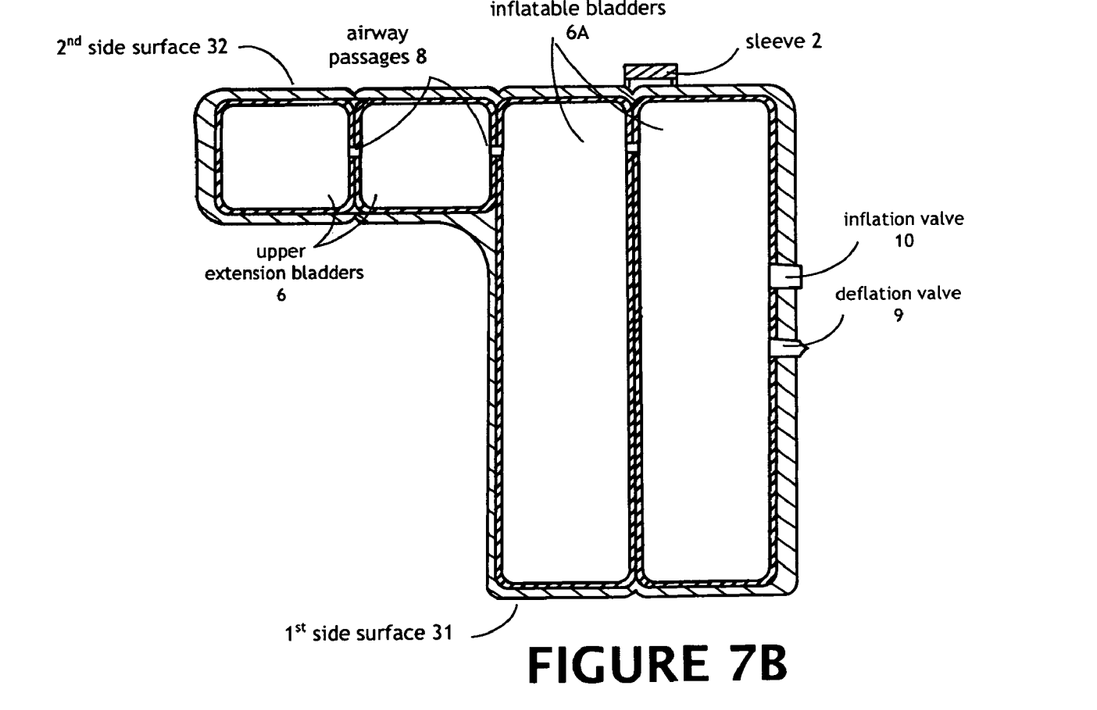

FIGS. 7A and 7B disclose still another preferred embodiment of the orthopedic support pillow of FIG. 6. FIG. 7A depicts a top view of the orthopedic support pillow, and FIG. 7B depicts a Section A-A taken through FIG. 7A. The orthopedic support pillow is comprised of four inflatable bladders that enable adjustment of firmness for comfort for the patient, two of the four inflatable bladders 6 having essentially square cross sections when taken axially, and the other two inflatable bladders 6A extending from the first side surface to the second side surface of the orthopedic support pillow. The inflatable bladders 6A are axially aligned with the support strap 2 and are each interconnected by airway passages 8.

Figure 8A:
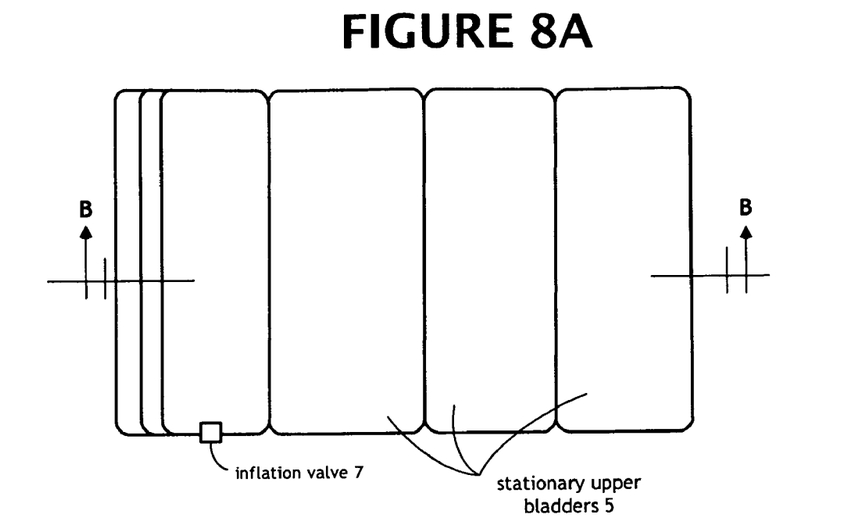
FIGS. 8A, 8B, and 8C disclose still yet another preferred embodiment of the multiple inflatable bladders of FIG. 6, FIG. 8A depicting the top view of the multiple inflatable bladders, FIG. 8B depicting a Section B-B taken through FIG. 7A, FIG. 8C being another perspective view of the multiple inflatable bladder configuration disclosed in FIGS. 8A and 8B, the multiple inflatable bladders being expandable and adjustable to accommodate differing sizes and shapes patients of varying heights and waist-size.
Figure 8B:
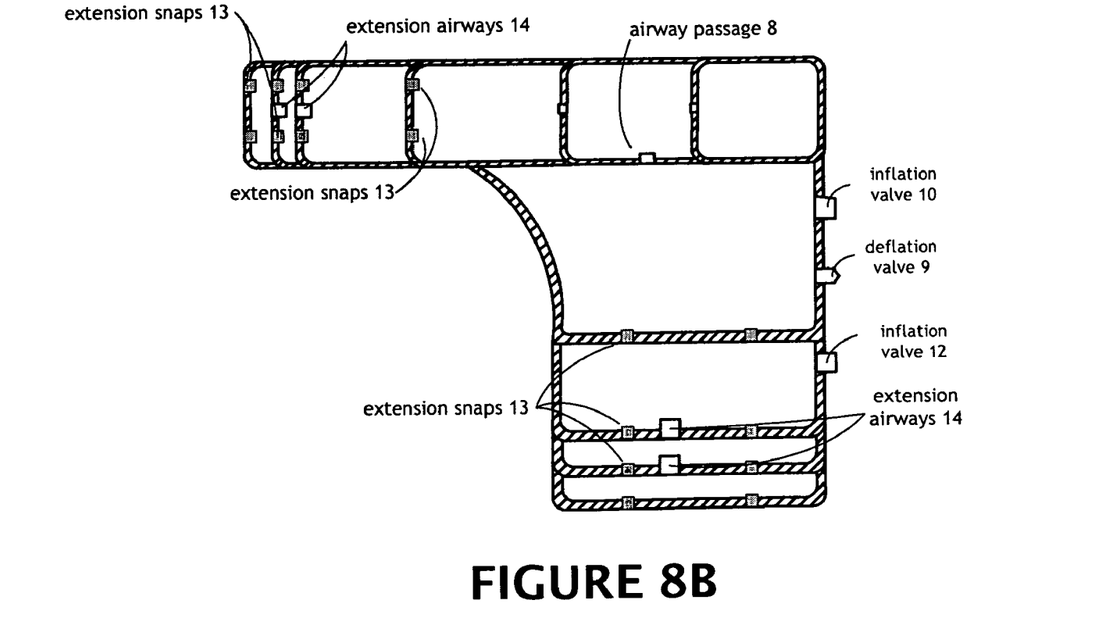
Figure 8C:
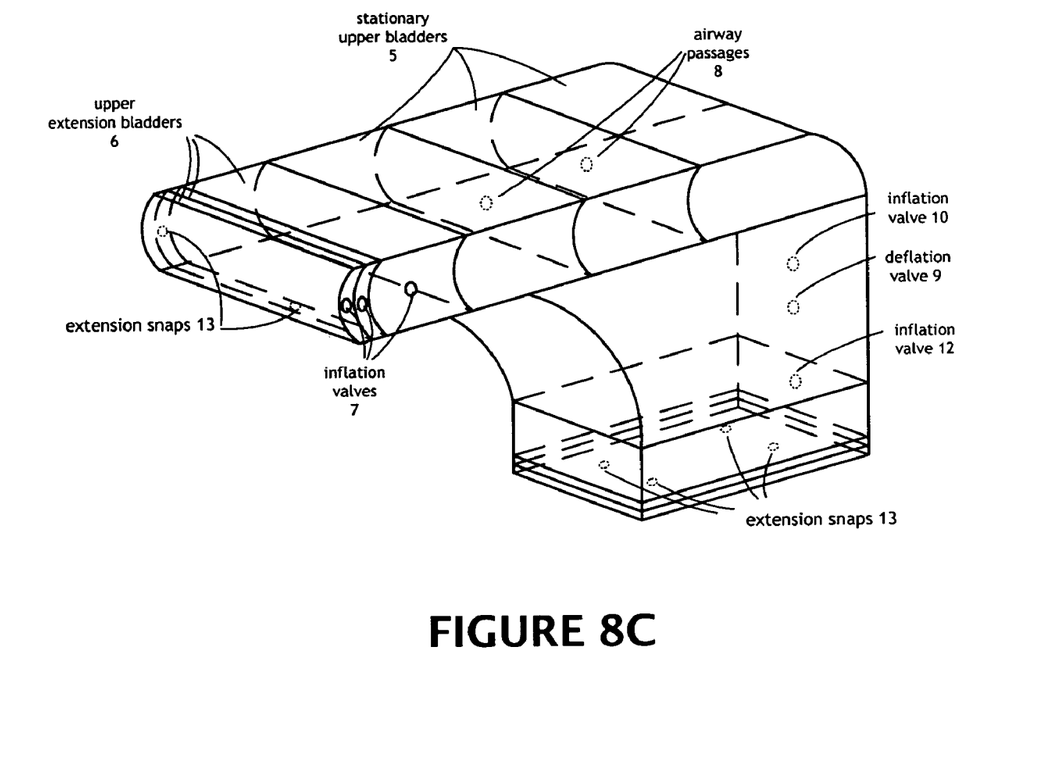

FIGS. 8A, 8B, and 8C disclose still yet another preferred embodiment of the multiple inflatable bladders of FIG. 6. FIG. 8A depicts the top view of the multiple inflatable bladders, and FIG. 8B depicts a Section B-B taken through FIG. 7A. FIG. 8C is another perspective view of the multiple inflatable bladder configuration disclosed in FIGS. 8A and 8B. The multiple inflatable bladders are expandable and adjustable to accommodate patients having various sizes and shapes. This embodiment enables the same orthopedic support pillow to be used by most patients, except for patients who are quite small or large.

The three stationary upper bladders 5 have essentially the same size, and the other upper bladder is an extension bladder 6, three extending positions being shown. Preferably, releasable fasteners are used to adjust the size of the upper extension bladder 6. The releasable fasteners may be snap fasteners having a first element and two second elements engageable with the first elements (not shown). If all of the upper extension snaps are secured together, only three upper bladders 5 are deployed. However, if air is circulated into the upper inflation valve 8, and the first set of extension snaps are released (see FIG. 8C), the upper extension bladder is deployed. The upper extension bladder can be enlarged by releasing another set of extension snaps. Similarly, a lower extension bladder section can be deployed by releasing the first set of extension snaps and by circulating air into the lower extension bladder 11. The lower extension bladder 11 can then be enlarged by releasing another set of lower extension snaps 13 and adding more air into the lower extension bladder valve.

Figure 9:
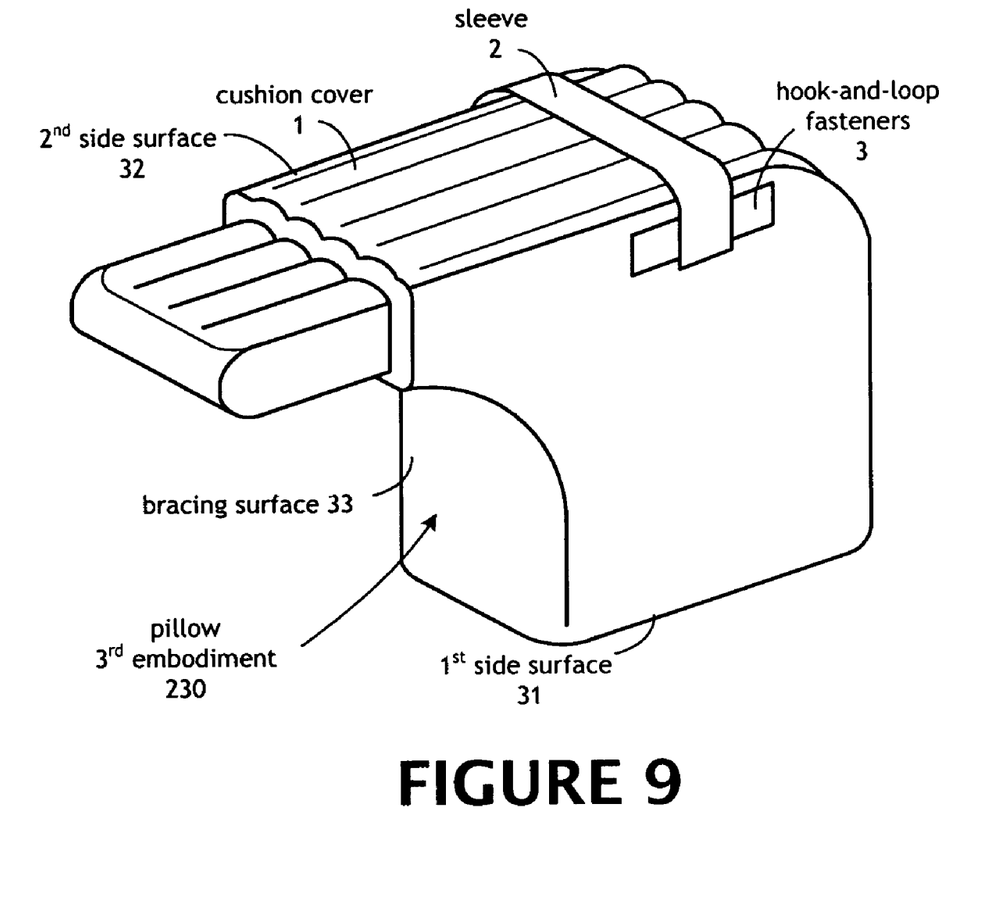
FIG. 9 discloses yet another preferred embodiment of the orthopedic support pillow of the present invention comprising an upper and a lower surface and a bracing surface with a strap positioned on the top surface for retaining a hand of a patient using the orthopedic support pillow, the orthopedic support pillow being comprised of multiple inflatable bladders that enable adjustment of firmness for comfort for the patient, the multiple inflatable bladders having bladder sections that traverse the axis of the support strap.
Figure 10A:
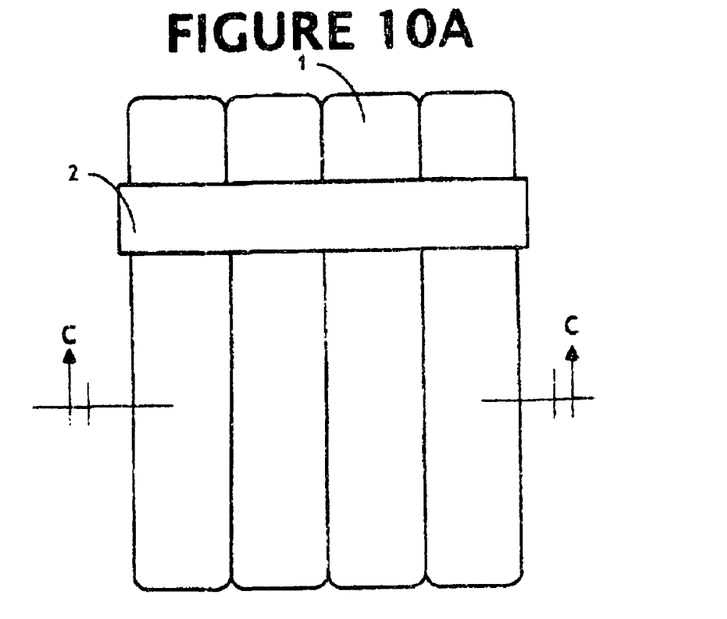
FIGS. 10A and 10B disclose the orthopedic support pillow of FIG. 9, FIG. 10A depicting the top view of the multiple inflatable bladders, FIG. 10B depicting a Section C-C taken through FIG. 10A.
Figure 10B:
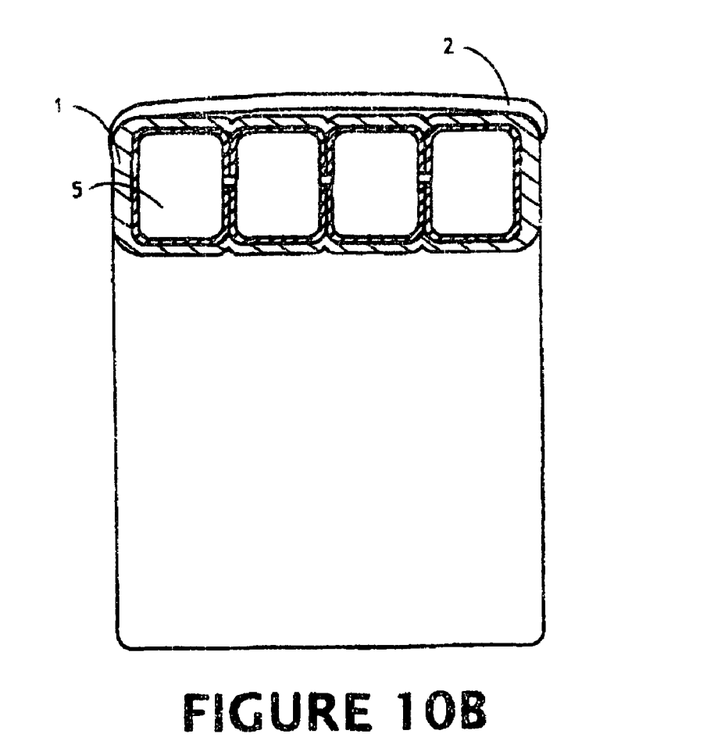
Figure 11A:
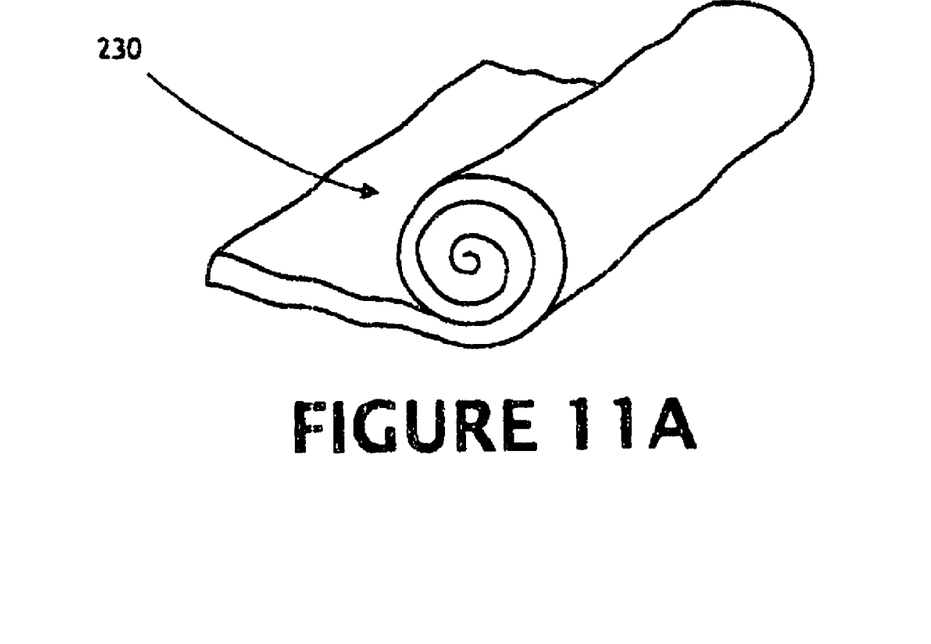
FIG. 11A is a schematic perspective view of the orthopedic support pillow of FIG. 6 or FIG. 9 rolled for storage in a compact condition when it is deflated.
Figure 11B:
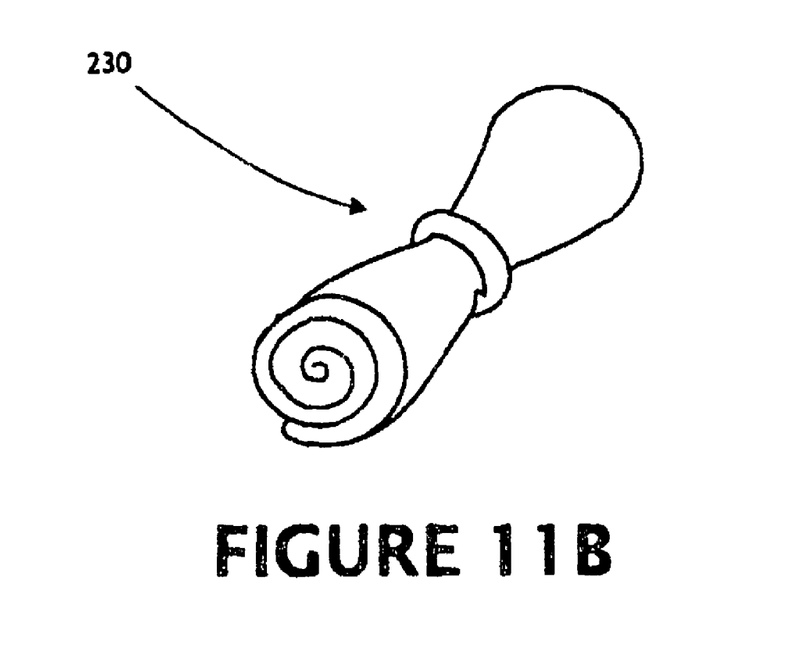
FIG. 11B is a schematic perspective view of the orthopedic support pillow of FIG. 6 or FIG. 9 rolled for storage in a compact condition when it is deflated, wrapped compactly in a support ring.

FIGS. 9, 10A, and 10B disclose yet another preferred embodiment of the orthopedic support pillow of the present invention 230. The orthopedic support pillow is comprised of multiple inflatable bladders 6 that enable adjustment of firmness for comfort for the patient, the multiple inflatable bladders 6 having bladder sections that traverse the axis of the support strap and are each interconnected by airway passages 8. FIGS. 10A and 10B disclose the orthopedic support pillow of FIG. 9, FIG. 10A depicting the top view of the multiple inflatable bladders. FIG. 10B depicts a Section C-C taken through FIG. 10A. FIGS. 11A and 11B are schematic perspective views of the orthopedic support pillow of FIG. 6 or FIG. 9 rolled for storage in a compact condition when it is deflated and stored or transported.

The resting surface 34 may be any flat surface that a patient may lie on—for purposes of illustration but not limited to—a cot, a bed, a sofa, a mattress, a car seat, the floor, or the ground.

The critical parameters in assuring that the orthopedic support pillow of the present invention will fit the body of a particular patient, are gender, height, weight, waist, and forearm length of the patient. The preferred embodiment of the orthopedic support pillow of the present invention is designed such that it can be used on either the right or left side of a patient. This is particularly important since many older patients having shoulder, elbow, or arthritis problems have similar problems on both sides of their bodies. Hence, such patients can use one orthopedic support pillow of the present invention to find relief. Also, the pillow can be used for supporting a retained arm when the patient sleeps on a side or on his or her back.

Throughout this Application, there are various Patents and a Provisional Application that are referenced by Patent number, Provisional Application number and inventor. The disclosures of these Patents and this Provisional Application are hereby incorporated by reference in their entireties into this specification in order to more fully describe the state-of-the-art.

It is evident that many alternatives, modifications, and variations of the present invention will be apparent to those skilled in the art in light of the disclosure herein. As the invention may be embodied in many forms without departing from spirit of essential characteristics thereof, it is expressly understood that the drawings are for purposes of illustration and description only, and are not intended as a definition of the limits of the invention. It is intended that the metes and bounds of the present invention be determined by the appended claim rather than by the language of the above specification, and that all such alternatives, modifications, and variations which form a conjointly cooperative equivalent are intended to be included within the spirit and scope of this claim.

PARTS LIST cushion cover 1
adjustable sleeve 2
hook-and-loop fasteners 3
firm memory foam 4
three stationary upper bladders 5
upper extension bladder 6.
multiple inflatable bladders 6
inflation valve 6
airway passages 8
upper inflation valve 8
lower extension bladder 11
inflation valve 12
set of lower extension snaps 13
extension airways 14
pocket 21
pocket stitching 22
$1^{st}$ preferred embodiment of orthopedic support pillow 30
first side surface 31
second side surface 32
bracing surface 33
resting surface 34
$3^{rd}$ preferred embodiment of orthopedic support pillow 130
$4^{th}$ preferred embodiment of orthopedic support pillow 230
$5^{th}$ preferred embodiment of orthopedic support pillow rolled for storage 330

I claim:
1. An orthopedic support pillow for use by a patient having an ailing arm while said patient is resting on one side in a generally prone position on a resting surface, said orthopedic support pillow comprising:
   a first side surface for positioning said orthopedic support pillow onto said resting surface;
   a second side surface opposing said first side surface, said second side surface retaining said ailing arm of said patient in an elevated position relative to said resting surface while said patient is resting in said generally prone position upon said resting surface; and
   a bracing surface between said first and second side surfaces, said bracing surface for abutment with an abdominal section of said patient when said patient is lying in said prone position on said one side;
   whereby said orthopedic support pillow provides stability and support to said ailing arm in said elevated position while said patient is lying in said generally prone position on said one side on said resting surface.

2. The orthopedic support pillow of claim 1, wherein said orthopedic support pillow can be used for a patient having said ailing arm being a left arm and said ailing arm being a right arm.

3. The orthopedic support pillow of claim 1, wherein a strap or pocket is positioned on said second side surface for retaining a hand of said ailing arm of said patient.

4. The orthopedic support pillow of claim 1, further comprising a cushion cover that is removable for cleaning or replacement, said orthopedic support pillow being made of a resilient foam material.

5. The orthopedic support pillow of claim 1, wherein said orthopedic support pillow has an inflatable pillow body with an interior that is adapted to be filled with a fluid to inflate said pillow body, said inflatable pillow body enabling firmness of said orthopedic support pillow to be adjusted for comfort for each patient.

6. The orthopedic support pillow of claim 1, wherein said second side surface has a width at least as great as a width of said ailing arm of said patient.

7. An orthopedic support pillow for use by a patient having an ailing arm while said patient is resting on one side in a generally prone position on a resting surface, said orthopedic support pillow including:
a side surface for accommodating said ailing arm of said patient in an elevated position relative to said resting surface while said patient is lying in said generally prone position upon said resting surface; and
a bracing surface near said side surface, said bracing surface for abutment with an abdominal section of said patient when said patient is resting in said prone position on said one side;
whereby said orthopedic support pillow provides stability and support to said ailing arm, said ailing arm resting in an elevated position on said side surface while said patient is lying in said generally prone position on said one side on said resting surface; and
whereby a hand of the ailing arm of said patient is retained by a retaining means across said side surface.

8. The orthopedic support pillow of claim 7, wherein a strap or pocket is positioned on said side surface for retaining a hand of said ailing arm of said patient.

9. The orthopedic support pillow of claim 7, wherein an inflatable pillow body has an interior that is adapted to be filled with a fluid to inflate said pillow body, said inflatable pillow body enabling firmness of said orthopedic support pillow to be adjusted for patient comfort, thereby adjusting support of said orthopedic support pillow provides over a range to said ailing arm.

10. The orthopedic support pillow of claim 7, further comprising a cushion cover that is removable for cleaning or replacement, said orthopedic support pillow being made of a resilient foam material.

11. The orthopedic support pillow of claim 7, wherein incremental inflation and deflation of a bladder is controlled from a control box, said control box being powered either by batteries or by plugging said control box into a standard wall outlet and powered by normal house current.

12. The orthopedic support pillow of claim 7, further comprising a manually operable control means for selectively discharging fluid into a fluid chamber for inflating a bladder and increasing height and firmness of said orthopedic support pillow and for selectively evacuating fluid from said fluid chamber deflating said bladder and thus decreasing height and firmness of said orthopedic support pillow, thereby adjusting support of said orthopedic support pillow provides over an entire range to said ailing arm.

13. The orthopedic support pillow of claim 7, wherein said orthopedic support pillow retains said ailing arm in an elevated position while said patient is lying in said generally prone position on said one side on said resting surface and said orthopedic support pillow retains said ailing arm near the shoulder, but only extends the forearm from the elbow to the hand away from the shoulder.

14. An orthopedic support pillow for use by a patient having an ailing arm while said patient is resting in a generally prone position on a resting surface on one side, said orthopedic support pillow including:
a bracing surface of said orthopedic support pillow abutting an abdominal section of said patient when said patient is lying in said prone position on said one side, and a side surface of said orthopedic support pillow for accommodating said ailing arm of said patient while said patient is lying in said generally prone position upon said resting surface;
whereby said orthopedic support pillow retains said ailing arm in an elevated position while said patient is lying in said generally prone position on said one side on said resting surface and said orthopedic support pillow retains said ailing arm near the shoulder, but only extends the forearm from the elbow to the hand away from the shoulder.

15. The orthopedic support pillow of claim 14, wherein size of the inflatable pillow body is adjustable to accommodate various size and shapes of patients.

16. The orthopedic support pillow of claim 14, wherein firmness of an inflatable pillow body is adjustable for patient comfort.

17. The orthopedic support pillow of claim 14, wherein a strap or pocket is positioned on said side surface for retaining a hand of said ailing arm of said patient.

18. The orthopedic support pillow of claim 14, wherein an inflatable pillow body has an interior that is adapted to be filled with a fluid to inflate said pillow body, said inflatable pillow body enabling firmness of said orthopedic support pillow to be adjusted for patient comfort, thereby adjusting support of said orthopedic support pillow provides over a range to said ailing arm.

19. The orthopedic support pillow of claim 14, further comprising a cushion cover that is removable for cleaning or replacement, said orthopedic support pillow being made of a resilient foam material.

20. The orthopedic support pillow of claim 14, wherein said orthopedic support pillow can be used for a patient having said ailing arm being a left arm and said ailing arm being a right arm.

* * * * *